United States Patent [19]

Balogh et al.

[11] Patent Number: 4,870,065
[45] Date of Patent: Sep. 26, 1989

[54] N-ALKYL OR N-ALKYLENE SUBSTITUTED GLYCIN AMIDES AS INSECTICIDES OR FUNGICIDES

[75] Inventors: Károly Balogh; Zsolt Dombay; Kroly Fodor; Erzsbet Grega ne Tth; Ernö Lörik; Magdolna Magyar née Tömörkényi; Jozsef Nagy; Károly Pásztor; Pál Sántha; Gyula Tarpai; István Tóth, all of Miskole; Eszter Urszin née Simon, Sajoóbá bony, all of Hungary

[73] Assignee: Eszakmagyarorszagi Vegyimuvek, Sajobabony, Hungary

[21] Appl. No.: 780,659

[22] Filed: Sep. 26, 1985

[30] Foreign Application Priority Data

Sep. 26, 1984 [HU] Hungary ............................... 3631/84
Jul. 24, 1985 [HU] Hungary ............................... 3631/84

[51] Int. Cl.⁴ ..................... A01N 57/02; A01N 43/00
[52] U.S. Cl. ..................................... 514/119; 514/79; 514/83; 514/89; 514/90; 514/91; 514/92; 514/93; 514/95; 514/99; 514/101
[58] Field of Search ..................... 514/118, 79, 83, 89, 514/90, 91, 92, 93, 95, 99, 101, 119; 558/171

[56] References Cited

FOREIGN PATENT DOCUMENTS 903304 1/1986 Belgium .
2194940 4/1986 United Kingdom ............... 558/171

*Primary Examiner*—Anton H. Sutto
*Attorney, Agent, or Firm*—Herbert Dubno; Jonathan Myers

[57] ABSTRACT

The present invention relates to novel compounds of the formula (I)

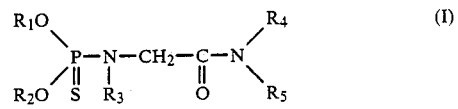

wherein $R_1$ and $R_2$ are the same or different and stand for alkyl having 1 to 4 carbon atoms optionally substituted by one or more halogen atoms, alkenyl having 2 to 6 carbon atoms, cycloalkyl having 3 to 6 carbon atoms, phenyl or lower alkoxy-alkyl group, $R_3$ stands for alkyl having 1 to 6 carbon atoms or alkenyl having 2 to 6 carbon atoms, $R_4$ and $R_5$ are the same or different and represent hydrogen, alkyl having 1 to 6 carbon atoms, alkenyl having 2 to 6 carbon atoms, cycloalkyl having 3 to 6 carbon atoms, phenyl, benzyl, phenyl substituted by one or more alkyl having 1 to 3 carbon atoms and/or by one or more halogen atoms, lower alkoxy-alkyl, a group of the formula $-(CH_2)_n-R_6$, wherein n is an integer between 0 to 3 and $R_6$ stands for a 3 to 7 membered saturated or unsaturated ring comprising 1 to 3 heteroatoms, said heteroatoms can be selected from the group of nitrogen and/or oxygen and/or sulphur, and $R_4$ and $R_5$ can together form with the adjacent nitrogen atom a hexamethylene-imino group.

The compounds of the invention exhibit acaricidal, insecticidal and fungicidal activity.

5 Claims, No Drawings

N-ALKYL OR N-ALKYLENE SUBSTITUTED GLYCIN AMIDES AS INSECTICIDES OR FUNGICIDES

TECHNICAL FIELD

The present invention relates to acaricidally, insecticidally and fungicidally active compounds, a process for the preparation thereof, compositions comprising the said compounds as active ingredient and their use for agricultural purposes.

The compounds of the invention are useful against mites, insects and fungal attack of grape, fruit plants, vegetables, bedding-plants and field crops.

The present invention therefore provides a N-alkyl- or N-alkenyl-N-(O,O-disubstituted-thiophosphoryl)-N',N'-disubstituted-glycinamides of the formula I

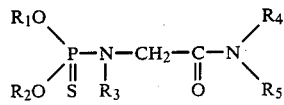

wherein $R_1$ and $R_2$ are the same or different and stand for alkyl having 1 to 4 carbon atoms optionally substituted by one or more halogen atoms, alkenyl having 2 to 6 carbon atoms, cycloalkyl having 3 to 6 carbon atoms, phenyl or lower alkoxy-alkyl group, $R_3$ stands for alkyl having 1 to 6 carbon atoms or alkenyl having 2 to 6 carbon atoms, $R_4$ and $R_5$ are the same or different and represent hydrogen, alkyl having 1 to 6 carbon atoms, alkenyl having 2 to 6 carbon atoms, cycloalkyl having 3 to 6 carbon atoms, phenyl, benzyl, phenyl substituted by one or more alkyl having 1 to 3 carbon atoms and/or one or more halogen atoms, lower alkoxy-alkyl, a group of the formula —$(CH_2)_n$—$R_6$, wherein n is an integer between 0 to 3 and $R_6$ stands for a 3 to 7 membered saturated or unsaturated ring comprising 1 to 3 heteroatoms, said heteroatoms can be selected from the group of nitrogen and/or oxygen and/or sulphur, and $R_4$ and $R_5$ can together form with the adjacent nitrogen atom a hexamethylene-imino group.

BACKGROUND ART

It is well-known in the art that the fruit plants (e.g. apple, cherry, plums) and certain vegetables (e.g. paprika, tomato) are significantly damaged by red spider mite (Tetranychus Telarius) and other different insects, e.g. green-flies, phytophagans, flies, moths. Great damage is also caused by different kinds of fungi, e.g. grey mould and downy mildew.

The plants are usually sprayed by different compositions against mites, E.g. Omite 57E comprising 57% of propargit [2-(p-tert.butylphenoxy)cyclohexyl-2-propynyl-sulphite] as active ingredient (referred to by Belgian patent specification No. 511,234 or German patent specification No. 705,037), or Rospin 25EC comprising 25% of chloropropylate [4,4'-dichloro-benzylacid isopropylester] as active ingredient (referred to by U.S. patent specifications Nos. 3,272,854 and 3,463,859) are widely known and used compositions. The Omite can be used for protecting winter apple, stone-fruits and grape exclusively after flowering in a dose of 1 to 2 l/ha, against red spider mite in a dose of 1 to 1.5 l/ha, against wide mite (Polyphagotarsonemus latus) in a dose of 1.8 to 2 l/ha in paprika. Rospin is effective against the moving forms of red spider mite in orchards and in grape in a dose of 2.5 to 4.5 l/ha.

Both compositions can control the red spider mite being resistant against compounds of phosphorus ester type with an efficacy of 70 to 100%. The drawback of their use is that relatively high doses have to be employed and they could not control the other pests or fungi of the orchards.

The pestiferous insects of pomiferous and berry fruits, grape, vegetables and field crops are controlled by phosphorus acid ester derivatives. E.g. a composition (Anthio 33EC) comprising 33% of formotion [O,O-dimethyl-S-(N-methyl-N-formyl-carbamoyl-methyl)-dithiophosphate] (described by U.S. Pat. Nos. 3,176,035 and 3,178,337) or Phosphothion 50 EC comprising 50% malathion [O,O-dimethyl-S-/1,2-dicarbetoxyethyl(-dithiophosphate]) referred to by U.S. Pat. No. 2,578,652) as active ingredient is employed. Both compositions are used against green-flies, phytophagans worms, flies and red spider mites in a dose of 2.8 to 3.2 l/ha and 1.2 to 1.5 l/ha, respectively. The drawback of these compositions is that relatively high doses have to be employed, they are toxic to bees and fishes, the red spider mites are resistant against them and e.g. tomato and plum cannot be treated with these compounds.

Grey mould being harmful to different crops can be well controlled by Sumilex 50 WP comprising 50% of procymidon [N-(3,5-dichlorophenyl)-1,2-dimethylcyclopropane-1,2-dicarboximide] (referred to by British patent specification No. 1,298,261 and U.S. patent specification No. 3,903,090) in a dose of 1.2 to 1.5 kg)ha.

SUMMARY OF THE INVENTION

Surprisingly we found that one part of the novel N-alkyl or N-alkenyl-N-(O,O-disubstituted-thiophosphoryl)-N',N'-disubstituted glycine amides possesses significant acaricidal effect, while others possesses weaker acaricidal, but significant insecticidal or fungicidal activity. The advantage of these compounds of the invention over the prior art compounds resides in that they can be used in more cultures, they are effective in substantially smaller doses, they can excellently control the red spider mites or other pestiferous insects, e.g. cotton bug, flies, moths being resistant against the compounds of the phosphorus acid ester type, and moreover they exhibit excellent fungicidal activity.

DETAILED DESCRIPTION OF THE INVENTION

The present invention therefore provides novel compounds of the formula I

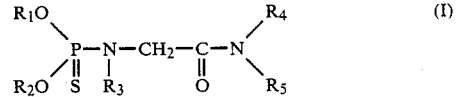

wherein $R_1$ and $R_2$ are the same or different and stand for alkyl having 1 to 4 carbon atoms optionally substituted by one or more halogen atoms, alkenyl having 2 to 6 carbon atoms, cycloalkyl having 3 to 6 carbon atoms, phenyl or lower alkoxy-alkyl group, $R_3$ stands for alkyl having 1 to 6 carbon atoms or alkenyl having 2 to 6 carbon atoms, $R_4$ and $R_5$ are the same or different and represent hydrogen, alkyl having 1 to 6 carbon atoms, alkenyl having 2 to 6 carbon atoms, cycloalkyl having 3 to 6 carbon atoms, phenyl, benzyl, phenyl substituted by one or more alkyl having 1 to 3 carbon atoms and/or one or more halogen atoms, lower alkoxy-alkyl, a group of the formula —$(CH_2)_n$—$R_6$, wherein n is an integer between 0 to 3 and $R_6$ stands for a 3 to 7 membered saturated or unsaturated ring comprising 1 to 3 heteroatoms, said heteroatoms can be selected from the group of nitrogen and/or oxygen and/or sulphur, and $R_4$ and $R_5$ can together form with the adjacent nitrogen atom a hexamethylene-imino group.

The novel compounds of the formula I according to the invention can be prepared by reacting a N-substituted-N',N'-disubstituted-glycinamide of the formula II

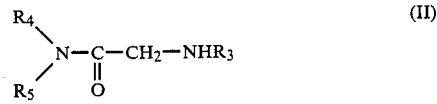

wherein the definitions of the substituents are the same as defined hereinabove, with a dialkoxy-thiophosphorous acid halide of the formula III

wherein the definitions of the substituents are the same as defined hereinabove, Hal stands for chlorine or bromine atom, optionally in a solvent, preferably benzene, toluene or chloroform, optionally in the presence of an acid-binding agent, preferably triethyl amine or dry pyridine at a temperature of 20° to 10° C., preferably 40° to 50° C. in a continuous or batch system, and recovering the end product from the reaction medium in a manner known per se.

The invention provides an acaricidal, insecticidal and/or fungicidal composition comprising a compound of the formula I as defined hereinabove in association with at least one carrier and a method of making such a composition which comprises bringing a compound of the formula I as defined ebove into association with at least one carrier. The composition of the invention comprises one or more compounds of the formula I in an amount of 5 to 95% by weight.

A carrier in a composition according to the invention is any material with which the active ingredient is formulated to facilitate application to the locus to be treated, which may for example be a plant, seed or soil, or to facilitate storage, transport or handling. A carrier may be a solid or a liquid including a material which is normally gaseous but which has been compressed to form a liquid and any of the carriers normally used in formulating pesticidal and fungicidal compositions may be used.

Suitable solid carriers include e.g. synthetic silicates, diatomaceous earth, talc.

Suitable liquid carriers include e.g. optionally halogenated hydrocarbons, aromatic hydrocarbons, dimethyl formamide.

Agricultural compositions are often formulated and transported in a concentrated form which is subsequently diluted by the user before application. The presence of small amount of a carrier which is a surface-active agent facilitates this process.

A surface-active agent may be an emulsifying agent, a dispersing agent or a wetting agent; it may be nonionic or ionic.

The compositions of the invention may for example be formulated as wettable powders, dusts, granules, solutions, emulsifiable concentrates, emulsions, suspensions, suspension concentrates. The emulsifiable concentrates, wettable powders and dusts are preferred.

The invention further provides a method of controlling pests and fungi, which comprises applying a compound or composition according to the invention in a sufficient amount to the plant.

The biological efficacity of the glycine amides of the formula I according to the invention was compared to that of the commercially available acaricidal compositions (Omite 57E/ Rospin 25EC), insecticidal compositions (Anthio 33EC, Phosphothion 50 EC) and fungicidal compositions (Sumilex 50 WP) in different cultures and against different pestiferous insects, mites and fungi. It was found that the novel glycine amides according to the invention can be successfully used for all the three purposes, their efficiency is the same as that of the commercial products, moreover in several cases their efficacy exceeds that of the commercial products.

The novel compounds of the invention, their preparation, formulation and biological activity are illustrated by the following, non-limiting examples.

EXAMPLE 1

To a 500 ml round-bottom flask equipped with a stirrer, thermometer and a feeding funnel 20.6 g N-ethyl-N'-ethyl-N'-phenylglycine amide are charged and dissolved in 200 ml of benzene under stirring.

11.0 g of triethyl amine, thereafter 18.85 g of O,O-diethylthiophosphorous chloride are added under stirring. After the addition the mixture is stirred for 2 hours at a temperature of 40° to 50° C. After the completition of the reaction the organic phase is washed with water, dried over anhydrous sodium sulphate and the benzene is distilled off.

28.5 g of N-ethyl-N-(O,O-diehtyl-thiophosphoryl)-N'-ethyl-N'-phenylglycine amide are obtained. $n_D^{20} = 1.5200$ Yield: 80%.

Purity (according to gas chromatographic analysis): 98.4%.

Elemental analysis: Calculated: N=7.82%; S=8.94%; Found: N=7.68%; S=9.06%.

EXAMPLE 2

To a 500 ml round-bottom flask equipped with a stirrer, thermometer and a feeding funnel 18.2 g of N-ethyl-N',N'-diallylglycine amide are charged and they are dissolved in a mixture of 200 ml of chloroform and 9 g of dry pyridine. 18.9 g of O,O-diethyl-thiophosphorous acid chloride are charged at room temperature under stirring, thereafter the reaction mixture is stirred at a temperature of 40° to 50° C. for 3 hours.

After the completition of the reaction the solution is extracted with water, the organic phase is dried over anhydrous sodium sulphate and the solvent is evaporated.

26.8 g of N-ethyl-N-(O,O-diethyl-thiophosphoryl)-N',N'-diallylglycine amide are obtained, $n_D^{20} = 1.4964$.

Yield: 78%.

Purity (according to gas chromatographic analysis): 96.8%.

Elemental analysis: Calculated: N=8.38%; S=9.58%; Found: N=8.64%; S=10.01%.

EXAMPLE 3

To a 500 ml round-bottom flask equipped with a stirrer, thermometer and dropping funnel 18.6 g of N-ethyl-N',N'-di-n-propyl-glycine amide are charged and dissolved in a mixture of 150 ml of toluene and 10.0 g triethyl amine. Thereafter, 18.9 g of O,O-diethyl-thiophosphorous chloride are added dropwise under stirring.

After completition of the addition the mixture is stirred at 2 hours at a temperature of 40° to 50° C., at the end of the reaction the organic phase is washed with water, dried over anhydrous sodium sulphate and the solvent is evaporated.

29.2 g of N-ethyl-N-(O,O-diethyl-thiophosphoryl)-N',N'-di-n-propyl-glycine amide are obtained. M.p.: 34°–35° C.

Yield: 88%.

Purity: (according to gas chromatographic analysis): 99.8%.

Elemental analysis: Calculated: N=8.28%; S=9.46%; Found: N=8.34%; S=9.51%.

EXAMPLE 4

The method of Examples 1 to 3 was followed and the compounds of the formula I listed in Table I were prepared.

TABLE I

| No. | $R_1$ | $R_2$ | $R_3$ | $R_4$ | $R_5$ | Physical constant M.p. (°C.) $n_D^{20}$ |
|---|---|---|---|---|---|---|
| 1. | ethyl | ethyl | ethyl | phenyl | methyl | 1.5254 |
| 2. | ethyl | ethyl | ethyl | phenyl | ethyl | 1.5200 |
| 3. | ethyl | ethyl | ethyl | phenyl | i-propyl | 1.5212 |
| 4. | ethyl | ethyl | allyl | allyl | hydrogen | 1.5273 |
| 5. | methyl | methyl | allyl | allyl | hydrogen | 1.5198 |
| 6. | chlorethyl | chlorethyl | allyl | allyl | hydrogen | 1.5228 |
| 7. | i-propyl | i-propyl | allyl | allyl | hydrogen | 1.5317 |
| 8. | ethyl | ethyl | ethyl | 2,6-diethyl-phenyl | hydrogen | 1.5250 |
| 9. | ethyl | ethyl | ethyl | 2,6-dimethyl-phenyl | hydrogen | 1.5264 |
| 10. | ethyl | ethyl | ethyl | 2-methyl-6-ethyl-phenyl | hydrogen | 1.5280 |
| 11. | ethyl | ethyl | ethyl | allyl | allyl | 1.4964 |
| 12. | ethyl | ethyl | methyl | n-propyl | n-propyl | 1.4838 |
| 13. | ethyl | ethyl | n-propyl | n-propyl | n-propyl | 1.4852 |
| 14. | ethyl | ethyl | i-propyl | n-propyl | n-propyl | 1.4844 |
| 15. | ethyl | ethyl | n-butyl | n-propyl | n-propyl | 1.4865 |
| 16. | ethyl | ethyl | i-butyl | n-propyl | n-propyl | 1.4868 |
| 17. | ethyl | ethyl | ethyl | n-propyl | n-propyl | 34–35 |
| 18. | methyl | methyl | ethyl | n-propyl | n-propyl | 1.5340 |
| 19. | chlorethyl | chlorethyl | ethyl | n-propyl | n-propyl | 1.5298 |
| 20. | i-propyl | i-propyl | ethyl | n-propyl | n-propyl | 1.5380 |
| 21. | ethyl | ethyl | allyl | n-propyl | n-propyl | 1.4952 |
| 22. | ethyl | ethyl | ethyl | cyclohexyl | hydrogen | 1.5120 |
| 23. | ethyl | ethyl | ethyl | hexamethylene | | 1.5335 |
| 24. | ethyl | ethyl | ethyl | 3-chlorphenyl | hydrogen | 1.5410 |
| 25. | n-butyl | n-butyl | ethyl | allyl | allyl | 1.5128 |
| 26. | i-butyl | i-butyl | allyl | allyl | allyl | 1.4632 |
| 27. | n-propyl | n-propyl | ethyl | allyl | allyl | 1.5294 |
| 28. | ethyl | ethyl | ethyl | 3,4-dichlorphenyl | hydrogen | 1.5482 |
| 29. | ethyl | ethyl | ethyl | cyclohexyl | methyl | 1.5224 |
| 30. | ethyl | ethyl | ethyl | benzyl | hydrogen | 1.5612 |
| 31. | ethyl | ethyl | ethyl | n-butyl | n-butyl | 1.5545 |
| 32. | ethyl | ethyl | ethyl | 4-tri-fluoromethyl-phenyl | hydrogen | 1.5335 |
| 33. | ethyl | ethyl | ethyl | 4-bromophenyl | hydrogen | 1.4948 |
| 34. | ethyl | ethyl | ethyl | 4-fluorophenyl | hydrogen | 1.4712 |
| 35. | ethyl | ethyl | ethyl | 4-methylphenyl | hydrogen | 1.4832 |
| 36. | allyl | allyl | ethyl | allyl | allyl | 1.6012 |
| 37. | phenyl | phenyl | ethyl | n-propyl | n-propyl | 1.5535 |
| 38. | cyclohexyl | cyclohexyl | ethyl | allyl | allyl | 1.5612 |
| 39. | methoxyethyl | methoxyethyl | ethyl | allyl | allyl | 1.5382 |
| 40. | ethoxyethyl | etoxyethyl | ethyl | n-propyl | n-propyl | 1.5410 |
| 41. | ethyl | ethyl | ethyl | 2,6-diethylphenyl | ethoxy-methyl | 1.5317 |
| 42. | ethyl | ethyl | ethyl | 2,6-di-ethylphenyl | methoxy-methyl | 1.5408 |
| 43. | ethyl | ethyl | ethyl | 2-methyl-6-ethylphenyl | ethoxy-methyl | 1.5322 |
| 44. | ethyl | ethyl | ethyl | 2,6-dimethylphenyl | 1,2,4-triazolyl-methyl | 1.5802 |
| 45. | c-propyl | c-propyl | methyl | c-propyl | 3-furyl | 1.5324 |
| 46. | dichlormethyl | dichlormethyl | ethyl | H | 2-furfuryl | 1.5296 |
| 47. | n-propyl | n-propyl | methyl | benzyl | 2-thienyl | 1.5304 |
| 48. | bromethyl | bromethyl | allyl | allyl | 2-thenyl | 1.5172 |
| 49. | allyl | allyl | n-hexyl | methyl | pyrrolidinyl | 1.6103 |
| 50. | ethenyl | ethenyl | allyl | allyl | pyranyl | 1.6182 |
| 51. | methoxy-methyl | methoxy-methyl | methyl | benzyl | pyridyl | 1.5407 |
| 52. | methyl | methyl | n-pentyl | methyl | 2-imidazolyl | 1.5148 |
| 53. | allyl | allyl | ethyl | ethyl | 2-imidazoline-4-yl | 1.5193 |
| 54. | phenyl | phenyl | methyl | methyl | oxazolyl | 1.5521 |
| 55. | ethyl | ethyl | ethenyl | H | thiadiazolyl | 1.5119 |
| 56. | methyl | methyl | n-pentyl | benzyl | piperidyl | 1.5026 |
| 57. | ethoxy-methyl | ethoxy-methyl | methyl | ethyl | morpholinyl | 1.5607 |

TABLE I-continued

| No. | R₁ | R₂ | R₃ | R₄ | R₅ | M.p. (°C.) $n_D^{20}$ |
|---|---|---|---|---|---|---|
| 58. | c-hexyl | c-hexyl | methyl | n-butyl |  | 1.6057 |
| 59. | ethyl | ethyl | n-pentyl | n-pentyl | 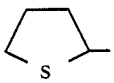 | 1.4875 |
| 60. | n-pentyl | n-pentyl | ethyl | ethyl | 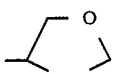 | 1.5132 |

EXAMPLE 5

Emulsifiable concentrate (10EC)

To a flask equipped with a stirrer 10 parts by weight of N-ethyl-N-(O,O-diethyl-thiophosphoryl)-N'-ethyl-N'-phenylglycine amide, 60 parts by weight of xylene, 22 parts by weight of dimethyl formamide, 5 parts by weight of octylphenyol polyglycol ether (Tensiofix AS) and 3 parts by weight of nonylphenol polyglycole ether (Tensiofix IS) are charged. The solution is stirred until it becomes clear, homogenized, thereafter filtered.

A composition comprising 10% of active ingredient is obtained.

Emulsion stability (in water of °dH 19.2 and in a concentration of 1%): it is stable after 2 hours.

After 24 hours reversible sedimentation occurred.

EXAMPLE 6

Emulsifiable concentrate (80EC)

To the apparatus according to Example 5, 80 parts by weight of N-ethyl-N-(O,O-diethyl-thiophosphoryl)-N',N'-diallyl-glycine amide active ingredient, 12 parts by weight of dichloromethane, 4 parts by weight of octylphenol polyglycol ether (Tensiofix AS) and 4 parts by weight of nonylphenol polyglycol ether (Tensiofix IS) are charged. The method of Example 5 is followed further on.

An EC composition with 80% of active ingredient content is obtained.

Emulsion stability (in a water of °dH 19.2 and in a concentration of 1%):
after 2 hours: reversible sedimentation
after 24 hours: reversible sedimentation.

EXAMPLE 7

Emulsifiable concentrate (50EC)

To the apparatus according to Example 5, 50 parts by weight of N-ethyl-N-(O,O-diethyl-thiophosphoryl)-N',N'-di-n-propyl-glycineamide active ingredient, 42 parts by weight of xylene, 5.6 parts by weight of alkylphenol polyglycole ether (Emulsogen IP-400) and 2.4 parts by weight of arylphenol polyglycol ether (Emulsogen EC-400) are charged. The method of Example 5 is followed further on. An EC composition with 50% active ingredient content is obtained.

Emulsion stability (in a water of °dH 19.2 and in a concentration of 1%):
after 2 hours: stable,
after 24 hours: minimal reversible sedimentation.

EXAMPLE 8

Dusting powder (5D)

To 20 parts by weight of synthetic silicate carrier with a grain size <40μ (Zeolex 444) 5 parts by weight of N-allyl-N-(O,O-di-i-propyl-thiophosphoryl)-N'-allylglycine amide active ingredient are sprayed in a blender. Thereafter 55 parts by weight of milled dolomite and 20 parts by weight of milled talc are added and the dust mixture is homogenized.

A dusting powder containing 5% of active ingredient is obtained.

Sieve residue on a sieve of DIN 100: 1.2%.

EXAMPLE 9

Dusting powder (10D)

To 20 parts by weight of a synthetic silicate carrier having high specific surface (Wessalon S) 10 parts by weight of N-methyl-N-(O,O-diethyl-thiophosphoryl)-N',N'-di-n-propyl-glycine amide active ingredient are sprayed under stirring in a blender. Thereafter 50 parts by weight of milled diatomaceous earth and 20 parts by weight of milled talc are added and the powder mixture is homogenized.

A dusting powder containing 10% active ingredient is obtained.

Sieve residue on a sieve of DIN 100: 0.95%.

EXAMPLE 10

Wettable powder (25 WP)

To 25 parts by weight of a synthetic silicate carrier of high specific surface 25 parts of weight of N-allyl-N-O,O-diethyl-thiophosphoryl-N'-allylglycine amide active ingredient are sprayed under stirring in a blender.

37 parts by weight of diatomaceous earth are homogenized with 2 parts by weight of aliphatic sulphonic acid sodium salt (Netzer IS) as wetting agent, thereafter this dust mixture is finely ground in an Alpine 100 LN mill of Ultraplex type. The grounded mixture thus obtained is homogenized with the previously prepared, homogenized, adsorbed active ingredient.

A wettable powder comprising 25% of active ingredient is obtained.

Floatability (in a concentration of 1%, in water of °dH 19.2 after 30 minutes): 82.7%.

EXAMPLE 11

Wettable powder (50 WP)

To 45 parts by weight of a synthetic silicate carrier of high specific surface (Wessalon 50) 50 parts by weight of N-allyl-N-(O,O-diethyl-thiophosphoryl)-N',N'-di-n-propylglycine amide active ingredient are sprayed in a blender. Thereafter 2 parts by weight of oleic-methyl-tauride sodium salt as wetting agent (Arkopon T) and 3 parts by weight of cresole-formaldehyde condensate (Dispergmittel 1494) as dispersing agent are added and the mixture is homogenized in the blender.

A wettable powder composition containing 50% of active ingredient is obtained.

Floatability (in a concentration of 1%, in a water of °dH 19.2 after 30 minutes): 84.2%.

EXAMPLE 12

Emulsifiable concentrate of mayonese consistency (5ME)

73 parts by weight of vaseline oil and 5 parts by weight of N-ethyl-N-[O,O-di-(chloroethyl)-thiophosphoryl]-N',N'-di-n-propylglycine amide active ingredient are homogenized by stirring.

In 20 parts by weight of water 2 parts by weight of fatty alcohol polyglycolether emulsifier (Gemopol X-080) are dissolved and the active ingredient diluted with the oil is added dropwise, very slowly under intensive stirring.

A mayonese-type concentrate, dilutable with water, having an active ingredient content of 5% is obtained.
Density- 0.942 g/ml.

EXAMPLE 13

Acaricidal activity against red spider mites (*Tetranychus urticae*)

Bean plants infected by red spider mites were induced to dry and fresh bean plants were placed in the neighborhood of the drying plants. The viable mites moved to the fresh beans within 1 day. These mites were used in the test.

Infestion: the 6th and 5th leaf with a short leaf-stalk of 4 weak-old bean plants were cut, thereafter 4×4 cm squares of the back surface of the leaf were encircled with a stripe of adeps lanae ointment additive.

To the isolated leaf surfaces 40 to 50 mites were applied from the freshly infected bean plants.

Arrangement of the test: Petri dishes of 10 cm diameter were lined with artificial-cotton discs and they were saturated with water.

Spraying: Compositions formulated as described in Examples 5 to 7, were diluted to an active ingredient concentration of 0.5% and 0.1% and the leaves were sprayed with these solutions four times.

The spraying was carried out by the aid of a laboratory sprayer working with compressed air.

The treated leaves were immediately placed to the above mentioned Petri disches lined with moistened artificial-cotton.

Evaluation: The percent mortality was measured after 48 hours calculated from the treatment. The percent mortality of the untreated controls was also taken into consideration as a correction.

Time of treatment: Feb. 14, 1983
Time of evaluation: Feb. 16, 1983.

The average temperature of air was 20° C., while the average humidity was 75%.

Results: The average results of four-four tests are listed in Table II wherein the number of the compounds is the same as listed in Table I.

TABLE II

| No. of the compound | Mortality in % | |
|---|---|---|
| | in a concentration of 1000 ppm | in a concentration of 5000 ppm |
| untreated control | 0 | 0 |
| 1. | 17 | 30 |
| 2. | 27 | 36 |
| 3. | 100 | 100 |
| 4. | 31 | 65 |
| 5. | 100 | 100 |
| 6. | 29 | 34 |
| 7. | 53 | 71 |
| 8. | 95 | 100 |
| 9. | 88 | 100 |
| 10. | 100 | 100 |
| 11. | 100 | 100 |
| 12. | 81 | 98 |
| 13. | 100 | 100 |
| 14. | 100 | 100 |
| 15. | 100 | 100 |
| 16. | 38 | 85 |
| 17. | 100 | 100 |
| 18. | 20 | 57 |
| 19. | 100 | 100 |
| 20. | 17 | 24 |
| 21. | 100 | 100 |
| 22. | 100 | 100 |
| 23. | 100 | 100 |
| 24. | 100 | 100 |
| 25. | 100 | 100 |
| 26. | 55 | 75 |
| 27. | 20 | 32 |
| 28. | 90 | 100 |
| 29. | 100 | 100 |
| 30. | 100 | 100 |
| 31. | 100 | 100 |
| 32. | 100 | 100 |
| 33. | 100 | 100 |
| 34. | 100 | 100 |
| 35. | 95 | 100 |
| 36. | 60 | 83 |
| 37. | 100 | 100 |
| 38. | 100 | 100 |
| 39. | 100 | 100 |
| 40. | 50 | 70 |
| 41. | 92 | 98 |
| 42. | 95 | 100 |
| 43. | 100 | 100 |
| 44. | 87 | 91 |
| 45. | 33 | 70 |
| 46. | 50 | 80 |
| 47. | 73 | 100 |
| 48. | 100 | 100 |
| 49. | 100 | 100 |
| 50. | 98 | 100 |
| 51. | 90 | 95 |
| 52. | 100 | 100 |
| 53. | 100 | 100 |
| 54. | 97 | 100 |
| 55. | 62 | 93 |
| 56. | 80 | 98 |
| 57. | 100 | 100 |
| 58. | 85 | 97 |
| 59. | 95 | 100 |
| 60. | 100 | 100 |
| Rospin 25EC | 100 | 100 |

It can be seen from the data of the above table that 44 from the 60 glycine amide derivatives are as effective as the widely used and known Rospin 25EC in both doses, 9 are almost as effective as Rospin 25EC, while only 7 are less effective, than Rospin 25EC. However, these latter ones possess significant insecticidal or fungicidal activity (see Examples 18, 19 and 20), while comparative formulation Rospin 25EC does not exhibit such an effect.

EXAMPLE 14

Dose dependant acaricidal activity

The experiment of Example 13 was carried out, but the solutions used were diluted to 1000 to 25 ppm.

Time of treatment: Jan. 26, 1984.
Time of evaluation: Jan. 28, 1984.

The average temperature of air was 22° C., while the average humidity was 75% in the course of the test.

Results: The serial number of the tested active ingredients, their concentration in the sprays and the percent mortality of red spider mites are summarized in Table III. The serial number of the compounds is the same as in Table I.

TABLE III

| Number of the compound | Percent mortality | | | | | | |
|---|---|---|---|---|---|---|---|
| | 1000 ppm | 500 ppm | 150 ppm | 125 ppm | 100 ppm | 50 ppm | 25 ppm |
| 3. | 100 | 100 | 100 | 100 | 100 | 96 | 92 |
| 13. | 100 | 100 | 98 | 98 | 96 | 95 | 94 |
| 14. | 100 | 100 | 100 | 100 | 100 | 100 | 96 |
| 15. | 100 | 100 | 100 | 100 | 100 | 98 | 98 |
| 17. | 100 | 100 | 100 | 100 | 100 | 100 | 100 |
| 21. | 100 | 100 | 100 | 99 | 98 | 95 | 71 |
| 22. | 100 | 100 | 98 | 96 | 93 | 90 | 85 |
| 23. | 100 | 100 | 100 | 93 | 92 | 90 | 90 |
| 24. | 100 | 100 | 96 | 94 | 88 | 85 | 70 |
| 29. | 100 | 100 | 99 | 97 | 94 | 92 | 90 |
| 30. | 100 | 100 | 98 | 95 | 93 | 90 | 88 |
| 31. | 100 | 100 | 100 | 100 | 100 | 100 | 98 |
| 32. | 100 | 100 | 97 | 95 | 90 | 87 | 80 |
| 33. | 100 | 100 | 96 | 93 | 89 | 86 | 75 |
| 34. | 100 | 100 | 98 | 96 | 92 | 90 | 87 |
| 37. | 100 | 100 | 100 | 96 | 90 | 85 | 80 |
| 38. | 100 | 100 | 100 | 100 | 100 | 100 | 100 |
| 39. | 100 | 100 | 100 | 100 | 100 | 100 | 100 |
| 43. | 100 | 100 | 97 | 95 | 93 | 90 | 90 |
| Rospin 25EC | 100 | 100 | 100 | 100 | 100 | 96 | 68 |
| Omite 57E | 100 | 100 | 100 | 100 | 100 | 15 | 12 |

It can be seen from the data of the above Table that the smallest effective concentration of the widely known and used Omite 57E composition is 100 ppm which cause 100% control of red spider mites, while in a concentration of 50 25 ppm it is practically ineffective. In contradiction, the use of the compounds of the invention can result in 70 to 100% mortality even in such a low concentration. The acaricidal activity of the compounds of the invention is the same or somehow better than that of the widely known and used Rospin 25EC.

EXAMPLE 15

Acaricidal activity in apple culture against red spider mite (*Panonychus ulmi* KOCH)

Experiments were carried out in a Jonathan apple-orchard planted in 1963 on a territory of 6×4 m in order to establish how effective the compositions of the invention are against mites in the apple culture.

The experiments were carried out in four replicates, the time of treatment was July 29, 1983. 1660 l/ha spary were used and concentration was 0.1% or 0.2%.

At the time of treatment a temperature of 25° C., a humidity of 55%, a force of wind of OB° and 0% cloudiness was measured. The evaluation was made on 1st Aug., 1983. The evaluation was carried out by counting the mites in each parcel on 5×20 leaves having almost the same surface. The efficacy was calculated by the Henderson-Tilton formula (efficacy=percent mortality):

$$\% \text{ mortality} = 100 \cdot \left/ 1 - \frac{Ta \cdot Cb}{Tb \cdot Ca} \right/$$

wherein

Ta=the number of the living mites at the time of evaluation (after treatment)
Tb=the number of the living mites before treatment
Ca=the number of the living mites on the untreated control leaves at the time of the evaluation
Cb=the number of the living mites on the untreated control leaves at the beginning of the experiment.

The compositions and experimental results are summarized in Table IV. The serial number of the compound corresponds to that of the Table I.

TABLE IV

| The number and dose of the compound | The number of the living mites on 5 × 20 leaves | | Mortality % |
|---|---|---|---|
| | before treatment | after treatment | |
| 11. 35EC spray of a concentration of 0.1% | 1106 | 699 | 29.8 |
| 11. 35EC spray of a concentration of 0.2% | 1234 | 242 | 78.2 |
| 17. 35EC spray of a concentration of 0.1% | 1172 | 70 | 93.4 |
| 17. 35EC spray of a concentration of 0.2% | 1093 | 45 | 95.4 |
| 25. 35EC spray of a concentration of 0.1% | 1025 | 646 | 30 |
| 25. 35 EC spray of a concentration of 0.2% | 1086 | 195 | 80 |
| 28. 35 EC spray of a concentration of 0.1% | 1100 | 69 | 93 |
| 28. 35EC spray of a concentration of 0.2% | 1027 | 46 | 95 |
| 35. 35EC spray of a concentration of 0.1% | 1053 | 47 | 95 |
| 35. 35EC spray of a concentration of 0.2% | 1108 | — | 100 |
| 39. 35EC spray of a concentration of 0.1% | 1201 | 649 | 40 |
| 39. 35EC spray of a concentration of 0.2% | 1075 | 174 | 82 |
| 41. 35EC spray of a concentration of 0.1% | 1098 | 642 | 35 |
| 41. 35EC spray of a concentration of 0.2% | 1113 | 150 | 85 |
| 42. 35EC spray of a concentration of 0.1% | 1250 | 34 | 97 |
| 42. 35EC spray of a concentration of 0.2% | 1236 | — | 100 |
| Anthio 33EC spray of a concentration of 0.2% | 1098 | 225 | 77.2 |
| Untreated control | 1131 | 1019 | — |

The data of the above table clearly show that while compounds Nos. 11, 25, 39 and 41 possess better or the same acaricidal activity in a concentration of 0.2% than the widely known and used Anthio 33EC used in the same concentration, then compounds Nos. 17, 28, 35 and 42 exhibit better acaricidal activity (over 93%) in a smaller concentration.

EXAMPLE 16

Acaricidal activity on plum against red spider mite

Similar experiment was carried out as in Example 15 by using plum plants planted in 1963 on a territory of 9×5 m in order to examine the efficacy of the spray comprising the compounds of the invention as active ingredient against red spider mite.

The 35EC compositions were diluted to an active ingredient concentration of 0.2%. The Anthio 33EC composition was sprayed in a dose of 890 l/ha. The treatment was carried out on 30th Aug., 1983. The weather conditions were as follows:

temperature: 21° C.
humidity: 67%
force of wind: 0 °B
cloudiness: 0%.

The evaluations were made on 30th August (before treatment), 2nd September (third day after treatment) and 6th September (seventh day after treatment).

The evaluations were carried out by counting the living mites in each parcel on 5×20 leaves having appropriately the same surface. The efficacy of the compositions was calculated by the Henderson-Tilton formula.

Results: The results of the experiments are summarized in Table V. The serial number of the compounds corresponds to that of Table I.

TABLE V

| Serial No. of the compounds | Number of the living mites on 5 × 20 leaves | | | Efficacy (%) | |
|---|---|---|---|---|---|
| | before treatment | on the 3rd day after treatment | on the 7th day after treatment | on the 3rd day | on the 7th day |
| 17. | 1190 | 30 | 26 | 96.3 | 96.8 |
| 19. | 1254 | 0 | 0 | 100 | 100 |
| 24. | 1097 | 10 | 0 | 100 | 100 |
| 28. | 1125 | 92 | 63 | 88.3 | 92.0 |
| 32. | 1200 | 57 | 42 | 93.0 | 95.0 |
| 33. | 1086 | 0 | 0 | 100 | 100 |
| 34. | 1138 | 0 | 0 | 100 | 100 |
| 44. | 1179 | 81 | 49 | 90.0 | 94.0 |
| Anthio 33EC | 1160 | 133 | 111 | 83.2 | 86.2 |
| Untreated control | 1259 | 862 | 880 | — | — |

It is clearly shown by the data of the above table that the glycine amide derivatives of the invention exhibit better acaricidal activity than the well-known and widely used, effective Anthio 33EC composition.

EXAMPLE 17

Acaricidal activity on apricot against Vasates sp. mite

An experiment similar to the experiment of Example 15 was carried out except that the compositions comprising the compounds of the invention as active ingredient was not sprayed onto the trees, but the solution was poured on to the soil around the trees. The well-known composition Rospin 25EC was used in the same manner.

The experiment was carried out in four replicates. The active ingredients were used in different concentrations. The efficacy was calculated on the basis of the Abbot formula as follows:

$$\text{efficacy } \% = \frac{C - T}{C} \cdot 100$$

wherein

C = the number of the living mites at the time of evaluation on the untreated plants T = the number of the living mites at the time of evaluation on the treated plants.

From the compounds of the invention N-ethyl-N-(O,O-diethyl-thiophosphoryl)-N',N'-di-n-propyl-glycine amide (No. 17) was used in different doses. The results of the experiments are summarized in Table VI.

TABLE VI

| No. of the compound | Concentration of the compound | Infection % | Efficacy % |
|---|---|---|---|
| 17. 25EC | 50 ppm | 5.4 | 82.6 |
| 17. 25EC | 100 ppm | 0.4 | 98.7 |
| 17. 25EC | 500 ppm | 0.4 | 98.7 |
| Rospin 25EC | 50 ppm | 13.6 | 56.1 |
| Rospin 25EC | 100 ppm | 1.8 | 94.2 |
| Untreated control | — | 31 | — |

It can be seen from the data of the above table that the composition according to the invention exhibits substantially higher acaricidal activity even in a concentration of 50 ppm than the well-known and widely used Rospin 25EC. These data also support that the compositions of the invention possess not only excellent contact, but excellent systemic effect as well.

EXAMPLE 18

Insecticidal activity against plum piercer

The insecticidal activity of the compounds of the invention was tested on plum plants in 1963 on a territory of 8×4 m against plum piercers. 3 trees were in one parcel. The trees were sprayed with a spray of an active ingredient content of 0.2% in a dose of 780 l/ha. The time and the weather conditions were as follows:

| Time | Temperature °C. | Humidity % | Force of wind B° | Cloudiness % |
|---|---|---|---|---|
| 1983. | | | | |
| May 17. | 24 | 56 | 0–1 | 0 |
| June 8. | 24 | 67 | 0 | 20 |
| July 6. | 23 | 65 | 0 | 0 |
| July 27. | 25 | 45 | 0 | 0 |
| August 9. | 22 | 55 | 0 | 0 |

The day of swarming was choosen as the day of treatment.

Time of evaluation: 26th Aug., 1983.

The efficacy of the compositions according to the invention was calculated by the Abbot formula.

Results: The number and the concentration of the active ingredients examined, the percent infection of the plum trees and the percent efficacy of the treatments are summarized in Table VII. The number of the compounds corresponds to that of the data of Table I.

TABLE VII

| No. of the compound | Infection % | Efficacy % |
| --- | --- | --- |
| 4. 35EC | 0.8 | 95.0 |
| 11. 35EC | 3.0 | 81.5 |
| 17. 35EC | 1.5 | 90.7 |
| 18. 35EC | 2.4 | 85.1 |
| 19. 35EC | 1.4 | 91.4 |
| 20. 35EC | 1.0 | 93.8 |
| 26. 35EC | 0 | 100.0 |
| 27. 35EC | 2.1 | 88.3 |
| 40. 35EC | 0.5 | 96.5 |
| 41. 35EC | 1.2 | 92.8 |
| 44. 35EC | 0 | 100.0 |
| Anthio 33EC | 2.7 | 83.3 |
| untreated control | 16.2 | — |

The data of the table demonstrate that in the same dose the compounds of the invention exhibit better insecticide activity than the well-known and widely used Anthio 33EC composition.

EXAMPLE 19

Insecticidal activity against fly and cotton bug

The insecticidal activity of the compounds of the invention against fly (*Musca domestica*) and cotton but (*Dysdercus cyngutatus*) were examined under laboratory conditions.

The compounds of the invention were used in a concentration of 0.1% and 0.2 ml were sprayed onto glass discs having a diameter of 85 mm. Phosphothion 50EC was used as control.

After the glass discs had dried, they were placed into Petri dishes, thereafter the test animals were introduced into the dish (10 animals in each dishes).

The mortality was measured after 24 hours calculated from the treatment.

The average temperature of the air was 20° C., while the average humidity was 75%.

Results: The number of the active ingredients tested and the percent mortality (the average value calculated on the basis of four tests) are summarized in Table VIII.

The number of the compounds corresponds to that of listed in Table I.

TABLE VIII

| No. of the compound | Mortality % Cotton bug | Fly |
| --- | --- | --- |
| 2. | 26 | 62 |
| 8. | 100 | 100 |
| 11. | 35 | 64 |
| 16. | 100 | 100 |
| 17. | 40 | 100 |
| 26. | 100 | 100 |
| 27. | 30 | 65 |
| 35. | 100 | 100 |
| 36. | 90 | 100 |
| 42. | 60 | 87 |
| 44. | 100 | 100 |
| Phosphotion 50EC | 100 | 100 |

It can be seen from the data of the table that the insecticidal activity of the compounds of the invention is similar or the same as that of the widely used Phosphotion 50EC employed under the same conditions.

EXAMPLE 20

Fungicidal activity

The fungicidal activity of the compounds of the invention was tested in a green-house. The examinations were carried out using the following funguses and plants:

| | |
| --- | --- |
| *Phytophtora infestans* | on tomato |
| *Botritis cynerea* | on faba bean |
| *Podosphera leucotricha* | on apple seed |
| *Uromyces appendiculatus* | on bean |
| *Colletotrichum leguminosarum* | on cucumber |
| *Erwinia caraptuvora* | on potato slice |
| *Erysiphe graminis* | on spring barley |

The experiment was carried out on 26th Jan., 1984. The above plants were preventively treated with the compositions according to the invention comprising 1000 ppm active ingredient, thereafter they were infected with the above fungi. The fungicidal activity was evaluated on the 5-9th day calculated from the infection. The evaluation was made by using the following scale:

0 = 0–25% fungicidal activity
1 = 25–50% fungicidal activity
2 = 50–75% fungicidal activity
3 = 75–90% fungicidal activity
4 = 90–100% fungicidal activity The scale was set up considering the drying of the leaves, rot of the leaves, the percentage covering of the leaves with the fungus and the ratio of the formation of thalluses.

The type of the compositions employed, the serial number of the active ingredient and the number characterizing the fungicidal activity are summarized in Table IX. The serial number of the compounds corresponds to that of listed in Table I.

TABLE IX

| Fungus | Fungicidal activity | | | | | | | | | |
| --- | --- | --- | --- | --- | --- | --- | --- | --- | --- | --- |
| | 4. 25WP | 7. 5D | 12. 10D | 17. 50EC | 21. 50WP | 26. 25WP | 27. 50WP | 36. 75EC | 40. 80EC | Sumilex 50WP |
| *Phytophtora infestans* | 0 | 2 | 0 | 1 | 2 | 2 | 0 | 1 | 0 | 0 |
| *Botritis cynerea* | 4 | 2 | 2 | 3 | 3 | 2 | 4 | 2 | 2 | 4 |
| *Podosphera leucotricha* | 4 | 3 | 4 | 3 | 3 | 3 | 3 | 2 | 2 | 1 |
| *Uromyces oppendiculatus* | 2 | 0 | 2 | 4 | 3 | 0 | 3 | 2 | 1 | 0 |
| *Colletotrichum leguminosarum* | 0 | 3 | 2 | 3 | 4 | 2 | 0 | 3 | 2 | 3 |
| *Erwinia caraptuvora* | 2 | 0 | 1 | 2 | 1 | 1 | 1 | 1 | 0 | 1 |
| *Erysiphe graminis* | 3 | 4 | 4 | 3 | 3 | 1 | 2 | 2 | 0 | 1 |

The data of the table show that the compositions according to the invention exhibit significant fungicidal activity and it exceeds the fungicidal activity of the widely known and used Sumilex 50WP in most cases.

EXAMPLE 21

Acaricidal activity on fruit trees against red spider mite

The experiments of Examples 15 and 17 were repeated in orchards planted in 1963, on Jonathan apple, pear and peach trees. The half of the trees was sprayed, the other half of the trees was sprinkled with the composition of the invention of an active ingredient concentration of 0.2% and 150 ppm, respectively.

The efficacy was calculated by the Abbot formula.

The compositions employed, the percent infection and the percent efficacy are summarized in Table X.

TABLE X

| No. | Compound concentration | Pear Infection % | Pear Efficacy % | Apple Infection % | Apple Efficacy % | Peach Infection % | Peach Efficacy % |
| --- | --- | --- | --- | --- | --- | --- | --- |
| 17. | 25EC 150 ppm | 0.4 | 97 | 0.4 | 98 | 0.4 | 98 |
|  | 0.2% spray | 0 | 100 | 0 | 100 | 0 | 100 |
| 25. | 25EC 150 ppm | 0.5 | 92 | 1.0 | 93 | 1.4 | 91 |
|  | 0.2% spray | 0.3 | 96 | 0.8 | 95 | 0 | 100 |
| 29. | 25EC 150 ppm | 0.5 | 90 | 0.9 | 94 | 0.6 | 95 |
|  | 0.2% spray | 0.1 | 99 | 0.4 | 98 | 0.5 | 96 |
| 32. | 25EC 150 ppm | 1.2 | 86 | 1.1 | 93 | 1.3 | 93 |
|  | 0.2% spray | 0.4 | 97 | 0.2 | 98 | 0.8 | 96 |
| 37. | 25EC 150 ppm | 0.3 | 98 | 0.4 | 97 | 0.7 | 94 |
|  | 0.2% spray | 0 | 100 | 0 | 100 | 0 | 100 |
| 43. | 25EC 150 ppm | 0.6 | 95 | 0.7 | 93 | 0 | 100 |
|  | 0.2% spray | 0 | 100 | 0 | 100 | 0 | 100 |

It is demonstrated by the data of the table that the compositions according to the invention exhibit significant contact and systemic acaricidal activity in the case of all the three kinds of fruit trees.

EXAMPLE 22

Acaricidal activity against grape mite (*Calepitrimerus vitis*)

Oporto grape was used in the experiment. The plants were treated at the time of budding (18th Apr. 1985) and at the stage of 3 to 5 leaflets (9th May, 1985). The compositions according to the invention were applied to the plants with 1000 l/ha of water in a dose of 1.2 l/ha and 1.8 l/ha.

As comparative composition Plictran 25WP comprising 25% of cihexatin [triciclohexyl-tin(IV)-hydroxide] was used in a dose of 1.8 kg/ha.

The evaluation was made before the flowering of grape (on 27th May, 1985) on 4×5 shoots. Each leaf on the shoots was rated according to the following numerical scale:

0 = no infection
1 = 0-20% infection (1 to 5 spots on the leaves)
2 = 21-40% (5 to 15 spots on the leaves, starting leaf distortion)
3 = 41-60% /15 to 25 spots on the leaves, increased distortion of the leaves)
4 = 61-80% (25 to 50 spots on the leaves, high distortion of the leaves, starting growth retardation)
5 = 81-100% (more than 50 spots on the leaves, the shoots' growth is highly retarded).

The infection index ($F_i$) was calculated on the basis of the above values as follows:

$$F_i = \frac{a_i \times f_i}{n}$$

wherein
$a_i$ = the value according to the above scale
$f_i$ = the frequency of one scale value
$n$ = the number of the all tested leaves.

The recorded data are presented in Table XI.

Simultaneously with the field evaluation, samples were collected for laboratory tests. Five leaves were cut calculated from the top of the plant. The mites were washed off from the collected 25 leaves using 0.1% Nonite solution in the laboratory, thereafter the solution was filtered through filter paper and the mites were counted under a microscope.

The efficacy was calculated according to the Abbot formula and the results as well as the number of the mites are presented in Table XI.

The serial number of the compounds corresponds to that of listed in Table I.

TABLE XI

| No. of the compound | Dose of the compound | Infection index $F_i$ | Number of the living mites on 25 leaves | Efficacy % |
| --- | --- | --- | --- | --- |
| 17. | 1.2 l/ha | 0.95 | 22 | 92 |
| 17. | 1.8 l/ha | 0.43 | 0 | 100 |
| 22. | 1.2 l/ha | 0.12 | 15 | 95 |
| 22. | 1.8 l/ha | 0.08 | 0 | 100 |
| 51. | 1.2 l/ha | 0.2 | 0 | 100 |
| 51. | 1.8 l/ha | 0.05 | 0 | 100 |
| 56. | 1.2 l/ha | 0.73 | 21 | 93 |
| 56. | 1.8 l/ha | 0.4 | 6 | 98 |
| Plictran 25WP | 1.8 kg/ha | 1.14 | 42 | 85 |
| untreated control |  | 2.4 | 291 | — |

It is shown by the data of the table that the compounds of the invention exhibit better acaricidal activity in both doses that the widely known and used Plictran 25WP composition.

EXAMPLE 23

Acaricidal activity against two-spotted spider mite

Oporto grape plants were treated with the compositions according to the invention on 14th May, 1985. 700 l/ha spray were used in a dose of 1.8 l/ha. Plictran 25WP was employed as comparative composition in the same dose.

The biological effect of the compositions was evaluated on the 3rd and 7th day after treatment on the basis of the infection of the treated and control leaves. The mite infection of the collected 5×20 leaves was determined by the aid of a mite brusher machine before the treatment and after the treatment on the 3rd and 7th day.

The percent efficacy was calculated on the basis of the Henderson-Tilton formula and summarized in Table XII.

and the efficacy was calculated on the basis of the Henderson-Tilton formula.

The serial number of the active ingredient, the number of the living mites (average of 3 tests) and the efficacy % are summarized in Table XIII.

TABLE XII

TABLE XIII

| No. of the compound | Number of the living mites | | | Efficacy % | |
|---|---|---|---|---|---|
| | before treatment mites/leaf | after treatment on the 3rd day | on the 7th day mites/leaf | on the 3rd day | on the 7th day |
| 17. | 38.59 | 0.16 | 0.28 | 99.46 | 99.76 |
| 30. | 38.59 | 0.02 | 0 | 99.93 | 100.0 |
| 32. | 38.59 | 0 | 0 | 100.0 | 100.0 |
| 38. | 38.59 | 0 | 0 | 100.0 | 100.0 |
| 45. | 38.59 | 2.97 | 12.2 | 90.2 | 85.0 |
| 47. | 38.59 | 0.48 | 4.37 | 98.4 | 96.5 |
| 51. | 38.59 | 0.88 | 8.75 | 97.1 | 93.0 |
| 56. | 38.59 | 0 | 2.5 | 100.0 | 98.0 |
| 58. | 38.59 | 3.94 | 4.62 | 98.7 | 96.3 |
| 59. | 38.59 | 0 | 0 | 100.0 | 100.0 |
| Danitol 10E | 38.59 | 4.20 | 9.02 | 85.96 | 92.57 |
| Untreated control | 38.59 | 29.93 | 121.52 | — | — |

| No. of the compound | 30 Efficacy % | |
|---|---|---|
| | on the third day | on the seventh day |
| 17. | 100 | 100 |
| 22. | 93 | 95 |
| 29. | 96 | 100 |
| 30. | 100 | 100 |
| 38. | 99 | 98 |
| 51. | 100 | 97 |
| 56. | 100 | 100 |
| Plictran | 88.4 | 91.9 |

It is shown by the data of the above table that the compositions according to the invention are more effective not only against leaf mites but two-spotted spider mites than the widely known and used Plictran 25WP.

EXAMPLE 24

Acaricidal activity on paprika against wide mite (*Polyphagotarsonemus latus*)

The wide mite damages paprika first of all, when its flowers fall dawn, the leaves and shoots become distorted, the crop narrowes, sometimes splits, the epidermis is suberized and the crop cannot be brought to the market. Therefore it is of great importance to defend against the attack of this mite.

"H₂" forced paprika plants (planted in a green-house on 10th Nov., 1984)(6.6 plants/m²) were treated with the compounds of the invention on 8th Mar., 1985.

The spraying was carried out using 1000 l/ha of water. The concentration of the active ingredient in the spray was 0.2%. Danitol 10E composition comprising 10% of fenpropatrin (α-cyano-3-phenoxybenzyl-2,2,3,3-tetramethyl-cyclopropane carboxylate) as active ingredient was used as comparative composition. The concentration of the solution used for spraying was 0.05%, while the dose was the same.

The temperature of the air was 27° C., while the humidity was 60% in the course of the test.

Before treatment and on the 3rd and 7th day after the treatment the living mites were counted on 3×25 leaves As it is demonstrated by the data of the above table the acaricidal activity of the compounds of the invention significantly exceeds that of the widely known and used Danitol 10E. The results of the evaluation on the 7th day show that the duration of action of the compounds is also excellent as the lifetime of the mite is very short /4–5 days/.

The main part of the mites are on the back surface of the leaves, which can be weakly covered by the spary in case of any manner of application. The good efficacy values indicate the suitable absorptin of the active ingredient as well.

EXAMPLE 25

Acaricidal activity against tomato leaf mite (*Aculops lycopersici*) on tomato plants The tomato leaf mite dameges the plants belonging to the family of solanaceae. It sucks the leaves, stem and the crop of tomato. The damaged leaf is yellowbrown, the back surface of the leaf becomes glossy like silver at the beginning, thereafter the foliage completely dries. This kind of mite is a novel parasite, therefore there was not any possibility to prevent its damages.

"Belcanto" forced tomato plants/planted to the green-house on 20th Jan., 1985//3.5 plants/m²/ were treated with the compositions according to the invention on 11th Mar., 1985. The spraying was carried out with a hand sprayer by using 1000 l/ha of a 0.2% water solution of the compounds according to the invention. Danitol 10E/see Example 24) was used as comparative composition in a concentration of 0.05% and in the same dose. The temperature was 25° C. at the time of treatment.

Before treatment and 24 hours and 3 days after the treatment the number of the living mites was counted on 5–5 leaves in each parcel and the efficacy was calculated on the basis of the Henderson-Tilton formula.

The serial number, the number of the living mites (an average of 3 replicates) and the percentile efficacy are summarized in Table XVI.

TABLE XIV

| No. of the compound | before treatment mites/leaf | Number of the living mites after the treatment | | Efficacy % after | |
|---|---|---|---|---|---|
| | | 24 hours mites/leaf | 3 days mites/leaf | 24 hours | 3 days |
| 17. | 299.3 | 3.46 | 10.0 | 99.08 | 97.19 |
| 29. | 299.3 | 0 | 0 | 100.0 | 100.0 |
| 40. | 299.3 | 22.5 | 23.53 | 94.15 | 93.40 |
| 43. | 299.3 | 0 | 0 | 100.0 | 100.0 |
| 45. | 299.3 | 40.38 | 52.5 | 89.5 | 85.3 |
| 47. | 299.3 | 8.65 | 7.14 | 97.75 | 98.0 |
| 51. | 299.3 | 6.53 | 11.78 | 98.3 | 96.7 |
| 54. | 299.3 | 0 | 0 | 100.0 | 100.0 |
| 56. | 299.3 | 3.46 | 7.5 | 99.1 | 97.9 |
| 57. | 299.3 | 0 | 0 | 100.0 | 100.0 |
| 58. | 299.3 | 3.61 | 6.78 | 99.06 | 98.1 |
| Danitol 10E | 299.3 | 9.53 | 15.33 | 97.46 | 95.70 |
| Untreated control | 299.3 | 376.66 | 356.86 | — | — |

It is demonstrated by the data of the table that the acaricidal activity of the compounds of the invention is similarly good or better against tomato leaf mite than that of the comparative composition Danitol 10E. As to the duration of action, the results of the third day have to be considered (and they are very good), as the lifecycle of this variety of mite is very short (2-3 days).

EXAMPLE 26

Acaricidal activity on cucumber against two-spotted spider mite (*Tetranychus telarius*)

"Tosca 69" cucumber plants planted to the greenhouse on 15th Feb., 1985 were treated on 12th Mar. 1985 when the plant had grown to 1 m, at the beginning of flowering. 1.2 plants were planted in a territory of 1m$^2$, the whole territory of the plants was 10 m$^2$. The spraying was carried out by using 1000 l/ha of 0.025 to 0.4% water-solutions of the compound of the invention No. 17. Plictran 25 WP (see Example 22) and Danitol 10E (see Example 24) were used as comparative compositions in different doses. The temperature was 22° C., the humidity was 75% at the time of treatment.

Before treatment and on the third, seventh, 14th and 21th day after the treatment 5×1 leaves were examined in each parcel by a binocular microscope. The number of the living mites was counted and the efficacy % was calculated on the basis of the Henderson-Tilton formula.

The compositions used and their doses, the number of the mites and the percentile efficacy are summarized in Table XV.

such a good and durable acaricidal activity even at a dose of 0.05 kg/ha, than the well-known and widely used other two compositions in a dose of 0.1 to 0.4 kg/ha.

If the composition comprising the compound No. 17 according to the invention as active ingredient is used in higher doses, its activity and duration of action highly surpass that of both Plictron 25WP and Danitol 10E.

EXAMPLE 27

Acaricidal activity on soy-bean against spider mite (*Tetranychus urticae* KOHC) being in different stages of development The experiments were carried out by using a mite strain obtained from carnation. According to our previous experiments this strain is resistant to dimethoate and chloropropylate and sensitive to amitroze, dienochlor and cihexatin. In the course of the observation 3566 moving mites, 2234 females, 251 deutonimphs, 390 larvaes and 4031 eggs were examined.

The simple spider mite was breeded on soybean plants.

The strips of the leaves infected with the mite strain to be examined were placed onto the uninfected plants. The spider mites quickly moved to the fresh soybean leaves.

The soybean leaves thus infected were kept in a chamber for 24 hours. Constant light, a temperature of 25±2° C. and a humidity of 90 to 95% was assured in order to promote the laying of the eggs and hatching.

After the time of laying eggs the leaves were cut from

TABLE XV

| No. of the compound | Dose of the compound kg/ha | No. of the living mites/leaf | | | | | Efficacy % after treatment | | | |
|---|---|---|---|---|---|---|---|---|---|---|
| | | before treatment | 3rd day | 7th day | 14th day | 21th day | 3rd day | 7th day | 14th day | 21th day |
| 17. | 0.025 | 457 | 338 | 651 | 745 | 1155 | 22.68 | 82.0 | 80.78 | 69.15 |
| | 0.05 | 469 | 352 | 24 | 346 | 826 | 21.54 | 99.36 | 91.30 | 78.59 |
| | 0.1 | 396 | 303 | 207 | 90 | 82 | 20.04 | 93.4 | 97.32 | 97.48 |
| | 0.2 | 111 | 43 | 0 | 0 | 1 | 59.51 | 100 | 100 | 99.9 |
| | 0.4 | 42 | 17 | 0 | 0 | 0 | 57.69 | 100 | 100 | 100 |
| Plictran | 0.05 | 159 | 124 | 195 | 549 | 195 | 18.47 | 84.67 | 40.72 | 84.67 |
| | 0.10 | 41 | 24 | 7 | 29 | 210 | 38.81 | 97.85 | 91.66 | 37.48 |
| | 0.40 | 14 | 5 | 0 | 39 | 16 | 62.67 | 100.0 | 67.15 | 86.05 |
| Danitol | 0.05 | 137 | 91 | 136 | 419 | 323 | 30.56 | 87.46 | 63.93 | 71.22 |
| | 0.1 | 312 | 202 | 183 | 191 | 412 | 32.32 | 92.59 | 92.78 | 82.71 |
| untreated control | | 115 | 110 | 910 | 975 | 942 | — | — | — | — |

It is demonstrated by the data of the above table that the composition comprising the compound No. 17 according to the invention as active ingredient can exhibit the plant and every form of mite was removed except eggs by a brush. Thus the age of the eggs being on the leaves are the same. The Petri dishes were placed to the chamber, thereafter the leaves carrying the protonimphs were placed into fresh leaves. Until they achive their sexual maturity the mites were bredded on living plants. Considering the day of the laying of the first eggs to be the first day, the matured, 3 to 5 days old female mites were used in the experiments.

The deutonimphs on the 10th, the protonimphs on the 8th, the larvae on the 6th and the eggs on the 1st and 5th day after laying eggs were treated with the solutions of the compound according to the invention No. 17 in different doses.

In the case of the moving form the strips of the infected leaves were placed again onto fresh leaves and the treatment with the acaricidal composition was carried out 2–3 hours after the moving of the mites.

When the eggs were examined, the females were removed before the treatment.

The leaf immersing method was used from the methods suggested by the FAO(BUSVINE, 1980) for judging the resistance. According to the said method six solutions (C.28%, 0.14%, 0.07%, 0.035%, 0.017% and 0.00875%) were prepared from the acaricidal active ingredient. In the course of treatment always the control solution containing only distilled water was the first, the most diluted solution the next, while the most concentrated solution was the last. The treatments were made in a room of a temperature of about 25° C. The infected and cut leaves were immersed for 10 seconds into the solution of a temperature of 22° C. under careful agitation. Thereafter the leaves were carefully shaken in order to remove the great droplets, then they were placed into a Petri dish onto moistened artificial cotton and the leaf edges were smeared with wool-fat in order to prevent the moving out of the mites. After the active ingredient had dried onto the leaves, the Petri dishes were placed into a chamber which was heated to a temperature of 24°±2° C. The dishes were lighted for 16 hours in a day with a light intensity of 800 lux. The relative humidity in the chamber was 90–95%. The evaluation was carried out under a stereomicroscope and the living and dead mites were counted. The 3 to 5 days old female mites on the 1st, 3rd and 7th day, the deutonimphs, protonimphs and larvae on the 1st and 3rd day after the treatment were tested.

When the ovicidal activity was evaluated, the ratio of the larvae (living and dead) hatched from the eggs and the ratio of proto- and deutimphs were evaluated separated.

When the contact residual activity of the compounds was examined soybean leaves were immersed into a 0.28% solution of the compound according to the invention No. 17. 4, 12, 24 and 48 hours after the treatment 3 to 5 days old female mites were placed onto the leaves. The evaluation was made on every day for 7 days.

The perishing of the control mites treated with distilled water was also considered. The mortality was calculated according to the Henderson-Tilton formula. The activity against the different forms of mite is summarized in Tables XVI, XVII and XVIII.

TABLE XVI

Activity of compound No. 17 against the moving forms of Tetranychus Urticae being in different stages of development

| Concentration | day of evaluation | 3–5 day old femalea Σ | living | mortality % | deutonymph living | mortality % | protonymph living | mortality % | larvae living | mortality % |
|---|---|---|---|---|---|---|---|---|---|---|
| control | 1. | 245 | 224 | | 19 | 18 | | 195 | 167 | | 55 | 51 | |
| | 3. | 245 | 174 | | 19 | 18 | | 195 | 165 | | 55 | 50 | |
| | 7. | 245 | 76 | | | | | | | | | | |
| 0.00875% | 1. | 280 | 98 | 62 | 97 | 3 | 97 | 381 | 2 | 99 | 186 | 3 | 98 |
| | 3. | 280 | 57 | 71 | 97 | 0 | 100 | 381 | 0 | 100 | 186 | 0 | 100 |
| | 7. | 280 | 30 | 65 | | | | | | | | | |
| 0.0175% | 1. | 298 | 17 | 94 | 75 | 0 | 100 | 75 | 0 | 100 | 149 | 0 | 100 |
| | 3. | 298 | 5 | 98 | 75 | 0 | 100 | 75 | 0 | 100 | 149 | 0 | 100 |
| | 7. | 298 | 0 | 100 | | | | | | | | | |
| 0.035% | 1. | 299 | 7 | 98 | 60 | 0 | 100 | 211 | 0 | 100 | 50 | 0 | 100 |
| | 3. | 299 | 1 | 99 | 60 | 0 | 100 | 211 | 0 | 100 | 50 | 0 | 100 |
| | 7. | 299 | 1 | 100 | | | | | | | | | |
| 0.07% | 1. | 431 | 2 | 99 | 80 | 0 | 100 | 154 | 0 | 100 | 25 | 0 | 100 |
| | 3. | 431 | 1 | 99 | 80 | 0 | 100 | 154 | 0 | 100 | 25 | 0 | 100 |
| | 7. | 431 | 0 | 100 | | | | | | | | | |
| 0.14% | 1. | 381 | 0 | 100 | 70 | 0 | 100 | 65 | 0 | 100 | 50 | 0 | 100 |
| | 3. | 381 | 0 | 100 | 70 | 0 | 100 | 65 | 0 | 100 | 50 | 0 | 100 |
| | 7. | 381 | 0 | 100 | | | | | | | | | |
| 0.28% | 1. | 396 | 0 | 100 | 85 | 0 | 100 | 50 | 0 | 100 | 30 | 0 | 100 |
| | 3. | 396 | 0 | 100 | 85 | 0 | 100 | 50 | 0 | 100 | 30 | 0 | 100 |
| | 7. | 396 | 0 | 100 | | | | | | | | | |

TABLE XVII

The activity of compound No. 17 against the eggs of *Tetranychus Urticae*

| Concentration | Time of the treatment | No. of individuals | No. of hatched larvae | No. of living moving ind. | Hatching in % | Survival % |
|---|---|---|---|---|---|---|
| control | 1st day after laying eggs | 542 | 502 | 487 | | |

TABLE XVII-continued

The activity of compound No. 17 against the eggs of *Tetranychus Urticae*

| Concentration | Time of the treatment | No. of individuals | No. of hatched larvae | No. of living moving ind. | Hatching in % | Survival % |
|---|---|---|---|---|---|---|
| 0.00875% | on the day before hatching | 414 | 408 | 406 | | |
| | 1st day after laying eggs | 235 | 89 | 73 | 41 | 35 |
| 0.0175% | on the day before hatching | 820 | 200 | 0 | 25 | 0 |
| | 1st day after laying eggs | 115 | 16 | 11 | 15 | 11 |
| 0.035% | on the day before hatching | 905 | 205 | 0 | 23 | 0 |
| | 1st day after laying eggs | 326 | 19 | 8 | 6 | 3 |
| 0.07% | on the day before hatching | 400 | 80 | 0 | 20 | 0 |
| | 1st day after laying eggs | 277 | 8 | 0 | 3 | 0 |
| 0.14% | on the day before hatching | 230 | 32 | 0 | 15 | 0 |
| | 1st day after laying eggs | 397 | 11 | 0 | 3 | 0 |
| 0.28% | on the day before hatching | 150 | 6 | 0 | 4 | 0 |
| | 1st day after laying eggs | 326 | 3 | 0 | 1 | 0 |
| | on the day before hatching | 196 | 0 | 0 | 0 | 0 |

The contact remaining activity of compound No. 17 against female *Tetranychus Urticae* in a 0.28% solution

| Placing onto the treated leaves | Time of evaluation (day) | No. of individuals | Living individual | Mortality % |
|---|---|---|---|---|
| 4 hours after treatment | 1 | 100 | 8 | 92 |
| | 2 | 100 | 3 | 97 |
| | 3 | 100 | 0 | 100 |
| | 4 | 100 | 0 | 100 |
| | 5 | 100 | 0 | 100 |
| | 6 | 100 | 0 | 100 |
| | 7 | 100 | 0 | 100 |
| 12 hours after treatment | 1 | 100 | 28 | 72 |
| | 2 | 100 | 10 | 90 |
| | 3 | 100 | 5 | 95 |
| | 4 | 100 | 2 | 98 |
| | 5 | 100 | 1 | 99 |
| | 6 | 100 | 1 | 99 |
| | 7 | 100 | 1 | 99 |
| 24 hours after treatment | 1 | 100 | 60 | 40 |
| | 2 | 100 | 39 | 61 |
| | 3 | 100 | 28 | 72 |
| | 4 | 100 | 15 | 85 |
| | 5 | 100 | 15 | 85 |
| | 6 | 100 | 15 | 85 |
| | 7 | 100 | 15 | 85 |
| 48 hours after treatment | 1 | 100 | 88 | 12 |
| | 2 | 100 | 69 | 31 |
| | 3 | 100 | 46 | 54 |
| | 4 | 100 | 34 | 66 |
| | 5 | 100 | 34 | 66 |
| | 6 | 100 | 34 | 66 |
| | 7 | 100 | 34 | 66 |

It is shown by the data of the above tables that the compound according to the invention No. 17 is a very quick and effective active ingredient which is able to control the different forms of Tetranychus urticae and its contact effect is also excellent.

EXAMPLE 28

Acaricidal activity against strawberry mite (*Tarsonemus pallidus* BANKS) on ornamental plants The first occurrence of strawberry mite was observed in Hungary in 1968, today it is the most harmful pest of strawberry. Since the middle of the 1970s it also damages ornamental plants, the damages increase years by years. Therefore the control of this pest is of great importance.

The experiments were carried out in the green-houses of the Municipal Botanic Garden. The compositions comprising the compounds of the invention as active ingredient were sprayed by the aid of a sprayer of Prskalica K-12 type in a dose of 2.8 l/ha. The temperature of the green-house was 21° C. at the time of the treatment. The following plants were treated:

*Saintpaulia ionantha* (the early symptoms of strawberry mite could be observed on the plant)
*Saxifraga sarmentosa* (the young leaves were highly distorted)
*Fittonia verschaffeltii* (the leaves slightly distorted).

The evaluation was made on the 3rd and 7th day calculated from the day of treatment. In both cases the 5-5 youngest leaves were cut from the test plants and the living and dead moving mites (female, male, larvae) were counted under a stereomicroscope in a laboratory. The strawberry mite always damages the young leaves of the plants only, it could not eat the older leaves.

The percent mortality was calculated on the basis of the living and perished mites. The results are summarized in Table XIX. The serial number of the compounds corresponds to the serial numbers in Table I.

TABLE XIX

| Plant | No. of the compound | Number of the mites | | | | | |
|---|---|---|---|---|---|---|---|
| | | 3rd day | | | 7th day | | |
| | | living (db) | dead (db) | mortality % | living (db) | dead (db) | mortality % |
| Saintpaulia | 17. | 5 | 385 | 98.72 | 1 | 250 | 99.6 |
| ionantha | 24. | 4 | 403 | 99.0 | 0 | 270 | 100 |
| | 33. | 0 | 390 | 100 | 1 | 198 | 99.4 |
| Fittonia | 17. | 2 | 220 | 99.0 | 0 | 370 | 100 |
| vershaffeltii | 19. | 0 | 374 | 100 | 0 | 396 | 100 |
| | 34. | 7 | 456 | 98.49 | 0 | 365 | 100 |
| Saxifraga | 17. | 14 | 309 | 95.66 | 6 | 271 | 97.83 |
| sarmentosa | 44. | 2 | 59 | 96.72 | 5 | 112 | 95.73 |
| | 58. | 6 | 214 | 97.27 | 12 | 351 | 96.70 |

It can be seen from the data of the table that the compositions according to the invention are also useful against strawberry mite.

EXAMPLE 29

Phytotoxicity of compound No. 17 on ornamental plants

The examination of phytotoxicity of the fungicidal and pesticidal agents is of great importance in growing of ornamental plants. The reason is on the one hand that the ornamental plants are of very different species and varieties, and their sensitivity to the chemicals are highly different, on the other hand that the green-house conditions are very favorable for the pests as well, therefore they can multiply at a much higher rate and their damage can significantly exceed the damage appearing on open fields. In order to avoid this damage the ornamental plants are treated much more times than the open field plants. There are known such kinds of ornamental plants, e.g. carnation or gerbera which are usually treated twice a weak with an acaricidal or insecticidal composition. The ornamental plant cultures are generally very valueable, therefore a very high amount of pesticidal agents is used considering the realtively small territory. Due to the chemical treatment the plants can be damages, therefore it seemed to be advisable to examine the phytotoxic activity of the compounds of the invention (compound No. 17). The experiments were carried out in the Botanic Garden of the "Eötvös Lóránd" University of Sciences and in the plantation of Rákosvölgy of the Municipal Gardening Company.

In the Botanic Garden the phytotoxicity of the compound No. 17 was examined on 90 different kinds of plants in two green-house having a great air-space and supplied with a shelter. Two treatments were carried out.

The first treatment was carried out on 31st, May, when a marked leaf of the selected plants was treated with an 50EC 0.3% emulsion of the compound No. 17. The treatment was carried out with a hand sprayer and a high amount of water was used. That part of the plant which was not required to be treated was covered. At the time of the teatment the temperature of the air in the green-house was 23° C., while the relative humidity was 80% and the temperature of the water used for spraying was 20.5° C.

The effect of the treatment was evaluated after two days, thereafter on each day. The treated leaves were compared to the other part of the plant and to the untreated plants of the same species.

The second treatment was carried out on the 5th of June, when the selected plants were sprayed using a high amount of spray and the surrounding plants were covered in order to avoid that the spray would reach them. The temperature and the humidity was 29° C. and 63%, respectively in the greenhouse at the time of spraying. The effect of the treatment was observed by controlling the plants in every two days. The tested plants species and the data relating to phytotoxicity are summarized in Table XX.

In the green-houses of the Municipal Gardening Company the examinations were carried out on plants being sensitive to the attack of spider mite (*Tetranychus urticae*), e.g. american carnation, gerbera and cala (*Zantadechia etiopica*) and cyclamen often damaged by cyclamen mite (*Tarsonemus pallidus*).

The american carnation and gerbera flowered at the time of treatment. Three varieties of the american carnation (Scania—red, Vanessa—violet, Pallas—yellow) were treated on a territory of 5 $m^2$. About 200 plants took part in the test.

The treatments were carried out at a temperature of 30° C. in a glass-house being free of shelter, in sunlight.

Two varieties of gerbera (B-6, Elegans—yellow, E-10—red and Symphonii—white) were treated.

The treatments were carried out in a glasshouse supplied with a roof shelter on a territory of 4 $m^2$ on 80 plants from each varieties. Buds, young and old flowers were simultaneously on the plants treated.

The temperature of air was 31° C., the relative humidity was 52% at the time of treatment.

The cyclamen and cala plants were treated on a territory of 1-1 $m^2$, respectively. The temperature and humidity were the same as in the case of the gerbera glasshouse.

The selected plants were treated on 4th June with a 0.3% solution of compound No. 17 (an 50EC composition). The temperature of water used in the experiment was 17° C.

The effect of the treatment was observed for 7 days following the day of treatment. The selected plants were compared to the plants being in the neighbouring untreated parcels. The flowers were not cut from the flowering plants during the time of the test in order to being able to observe the probable phytotoxic symptoms on the petals too.

The plant species examined and the data relating to phytotoxicity are summarized in Table XX. The mark "—" indicated that no phytotoxic symptom has appeared, while "+" indicates the presence of phytotoxic symptoms.

TABLE XX

| Family | Plant species varieties | Result of the leaf-treatment on the 4th day | Result of the plant-treatment on the 7th day |
|---|---|---|---|
| Araceae | 23 different kinds | − | − |
| Bromeliaceae | 6 different kinds | − | − |
| Polypodiaceae | 4 different kinds | + | + |
|  | 2 different kinds | − | − |
| Aspidiaceae | Dryopteris sp. | + | + |
| Urticaceae | Pilea cadieri | − | − |
| Nytaginaceae | Pisonia brunoniana | − | − |
| Maranthaceae | 6 different kinds | − | − |
| Acanthacea | 5 different kinds | − | − |
| Euphorbiaceae | 4 different kinds | − | − |
| Aralicaeae | 5 different kinds | − | − |
| Rubiaceae | Hoffmannia giesbrechtii | − | − |
| Verbenaceae | Lantana Camara | − | − |
| Compositae | 2 different kinds | − | − |
| Passifloraceae | Passitlora warmingii | − | − |
| Moraceae | 4 different kinds | − | − |
| Gesneriaceae | Streptocarpus sp. | − | − |
| Piperacaea | Peperomia feli | − | − |
| Oxalidaceae | Oxalis sp. | − | + |
| Caricaceae | Carica papaya | + | + |
| Palmae | 3 different kinds | − | − |
| Liliaceae | 4 different kinds | − | − |
| Amaryllidaceae | Alstroemeria aurantiaca | − | − |
| Agavaceae | 4 | − | − |
| Zingiberaceae | Hedychium gardnerianum | − | − |
| Lauraceae | Persea americana | − | − |
| Malvaceae | 2 | − | − |
| Balsaminaceae | Impatiens valeriana | − | − |
| Pandanaceae | 2 | − | − |

From the 90 species or varieties of plants belonging to 28 plant families 7 species have shown phytotoxic symptoms. The most conspicious symptoms could be observed on some fern species, e.g. Nephrolepis, Dryopteris species and *Asplenium nidus*.

In the case of these plants the edge of the leaf become clear at the beginning and it dried soon.

Soon after the treatment phytotoxic symptoms could be observed on the edge and top of the leaf of Carica papaya. It become oedematously transparent, thereafter these oedematous spots become white and dried.

When the whole plant was treated, these symptoms could also be observed. In the case of Oxalis sp. the spraying of the leaf has not resulted in phytotoxic symptoms, while 7 days after the treatment of the whole plant the edges of the leaves become oedamatously transparent and dried.

The extent of the phytotoxic symptoms was not so high that it would jeopardize their further development even in the case of these sensitive plants.

If the leaves had been sprayed, the burnt—if there was any—could be observed only on the sprayed leaf. The phytotoxic effect did not spread to the older or younger leaves.

The plants being in the table, showing phytotoxic symptoms are not host plants of the spider mite (Tetranychus urticae).

In the course of the treatment carried out on the plantation of the Municipal Gardening Company the examined varieties of american carnation did not show any phytotoxic symptom both on the leaves or on the flowers. This also stands for the cala (*Zantadeschia etiopica*) and cyclamen (*Cyclamen persicum*). The leaves of the tested four varieties of gerbera showed no phytotoxic symptom. However, the old, over-developed flowers of varieties E-10 (red flower) and Symphonii (white flower) light phytotoxic symptoms could be observed. This means that the edge or the surface of the petal slightly colored to yellow.

The change of color was not followed by formation of necrotic lesions. The young flowers did not show this symptom.

It can be established that the composition comprising the compound of the invention No. 17 can be advantageously employed on ornamental plants against pestinferous mite varieties.

What we claim is:

1. An acaricidal method of treatment which comprises the step of applying to a plant site in need of said treatment, a pesticidally effective amount of a compound of the Formula (I)

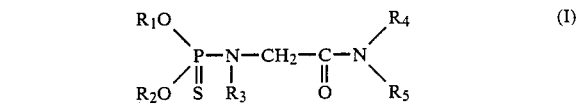

wherein $R_1$ and $R_2$ are the same or different and stand for alkyl having 1 to 4 carbon atoms unsubstituted or substituted by at least one halogen atom, alkenyl having 2 to 6 carbon atoms, cycloalkyl having 3 to 6 carbon atoms, phenyl or lower alkoxyalkyl group, $R_3$ stands for alkyl having 1 to 6 carbon atoms or alkenyl having 2 to 6 carbon atoms, $R_4$ and $R_5$ are the same or different and represent hydrogen, alkyl having 1 to 6 carbon atoms, alkenyl having 2 to 6 carbon atoms, cycloalkyl having 3 to 6 carbon atoms, phenyl, benzyl, phenyl substituted by at least one alkyl having 1 to 3 carbon atoms, by at least one trifluoromethyl group or by at least one halogen atom, or are lower alkoxyalkyl, 1,2,4-triazolyl-methyl, 3-furyl, 2-furfuryl, 2-thienyl, 2-thenyl, pyrrolidinyl, pyranyl, pyridyl, 2-imidazolyl, 2-imidazolin-4-yl, oxazolyl, thiadiazolyl, piperidyl, morpholinyl, dimethyleneimino, 2-tetrahydrothienyl, and 5-(1,3-dioxolanyl), or $R_4$ and $R_5$ can together form with the adjacent nitrogen atom a hexamethyleneimino group.

2. The acaricidal method of treatment defined in claim 1 wherein in the compound of the Formula (I)

$R_1$ and $R_2$ are the same or different and stand for alkyl having 1–4 carbon atoms unsubstituted or substituted by one or more halogen atoms, $R_3$ stands for alkyl having 1–6 carbon atoms or alkenyl having 2–6 carbon atoms, $R_4$ and $R_5$ are the same or different and stand for hydrogen, alkyl having 1–6 carbon atoms, alkenyl having 2–6 carbon atoms, cycloalkyl having 3–6 carbon atoms, phenyl, benzyl or phenyl substituted by at least one alkyl having 1–3 carbon atoms or by at least one halogen atom.

3. The acaricidal method of treatment defined in claim 1 wherein the compound of the Formula (I) is N-ethyl-N-(O,O-diethyl-thiophosphoryl)-N',N'-di-n-propyl-glycine amide.

4. The acaricidal method of treatment defined in claim 1 wherein the compound of the Formula (I) is applied to a plant site where the red spider mite is present.

5. The acaricidal method of treatment defined in claim 1 wherein the compound of the Formula (I) is applied to a plant site where the Vasates spider mite is present.

* * * * *